| United States Patent [19] | [11] 3,978,079 |
|---|---|
| Bollyky et al. | [45] Aug. 31, 1976 |

[54] CHEMILUMINESCENCE

[75] Inventors: Laszlo Joseph Bollyky; Robert Henry Weitman, both of Stamford, Conn.

[73] Assignee: American Cyanamid Company, Stamford, Conn.

[22] Filed: July 24, 1974

[21] Appl. No.: 491,450

Related U.S. Application Data

[60] Continuation of Ser. No. 223,793, Feb. 4, 1972, abandoned, which is a division of Ser. No. 886,395, Dec. 12, 1969, abandoned, which is a continuation-in-part of Ser. No. 547,761, May 5, 1966, abandoned.

[52] U.S. Cl. .................. 260/326 N; 260/239 BF; 260/243 R; 260/293.63; 260/293.76; 260/293.86; 260/293.87; 260/293.88; 260/294.8 E; 260/295 R; 260/295 T; 260/295 AM; 260/304 R; 260/306.8 R; 260/308 A; 260/326.26; 260/326.42; 260/347.3; 260/479 S; 260/481 R; 260/482 R; 260/551 P; 260/551 S; 260/558 R; 260/559 A; 260/561 A; 260/561 K; 260/562 N; 260/562 S; 260/562 K; 260/566 AE; 260/583 DD; 252/301.3 R

[51] Int. Cl.² ............... C07D 209/48; C07D 207/40

[58] Field of Search ....... 260/326 N, 326 A, 326.42, 260/326.4, 326.26

[56] References Cited

UNITED STATES PATENTS

| 3,301,826 | 1/1967 | Towney .................. 260/326.26 |
| 3,306,902 | 2/1967 | Wolf et al. .................. 260/326.42 |

OTHER PUBLICATIONS

Emeleus et al., "J. Chem. Soc." (A), 1969: 431–433 (1969).

*Primary Examiner*—Lewis Gotts
*Assistant Examiner*—S. P. Williams
*Attorney, Agent, or Firm*—Charles J. Fickey; Gordon L. Hart

[57] ABSTRACT

Novel O-oxalylhydroxyl-amine compositions of matter and reactions and to the direct generation of light from chemical energy employing such compositions. By "light" as referred to herein is meant electromagnetic radiation at wavelengths falling between about 350 m$\mu$ and 800 m$\mu$. Disclosed compounds include diphthalimide oxalate, disuccinimido oxalate, and dimaleimido oxalate.

3 Claims, No Drawings

CHEMILUMINESCENCE

This is a continuation of our copending application Ser. No. 223,793, filed Feb. 4, 1972 and now abandoned, which was a division of application Ser. No. 886,395, filed Dec. 12, 1969, now abandoned which was a continuation-in-part of application Ser. No. 547,761, filed May 5, 1966 and now abandoned.

The present invention relates to novel O-oxalylhydroxyl-amine compositions of matter and reactions and to the direct generation of light from chemical energy employing such compositions. By "light" as referred to herein is meant electromagnetic radiation at wavelengths falling between about 350 m$\mu$ and 800 m$\mu$.

The art of generating light from chemical energy, i.e., chemiluminescence, is continually in search of compositions which when reacted substantially improve the intensity and lifetime of light emission as contrasted to known chemiluminescent compositions and reactions. Obviously, improved compositions are constantly in demand for use as signal devices, for area illumination, etc.

It is an object of this invention to obtain a chemiluminescent compositions and a process employing said composition whereby a high efficiency may be obtained in the conversion of chemical energy into light.

Another object is to obtain a chemiluminescent compound which produces light over an extended period of time.

Another object of this invention is to obtain a chemiluminescent composition which attains light of substantially higher intensity than has been obtained with former chemiluminescent compositions.

Another object of this invention is to obtain a chemiluminescent composition which may be employed to obtain light by a process which is mechanically simple and which is economically inexpensive.

Another object of this invention is to obtain a chemiluminescent reactant which is stable over a long period of time and which may be subsequently reacted to obtain chemiluminescent light.

Another object of this invention is to obtain a chemiluminescent reactant which when reacted will obtain chemiluminescent light by a process which is not hazardous.

The term "chemiluminescent reactant", as used herein, means (1) a mixture which will result in a chemiluminescent reaction when reacted with other necessary reactants in the processes as disclosed herein, or (2) a chemiluminescent composition.

The term "fluorescent compound", as used herein, means a compound which fluoresces in a chemiluminescent reaction, or a compound which produces a fluorescent compound in a chemiluminescent reaction.

The term "chemiluminescent composition", as used herein, means a mixture which will result in chemiluminescence.

The term "admixing", as used herein, means "reacting" or sufficiently bringing together component reactants to obtain a chemiluminescent reaction.

The term "hydroperoxide compound" as used herein is limited to peroxide compounds having at least one "HOO—" group, or a compound which upon reaction produces a compound with such a group.

The term "peroxidic groups", as used herein, represents "HOO—", "ROO—", or

where R is an organic substituent, such as alkyl, cycloalkyl, $\alpha$-hydroxyalkyl, substituted alkyl, for example.

The term "diluent", as used herein, means a solvent or a vehicle which when employed with a solvent does not cause insolubility.

The term "peroxide compound", as used herein, also includes compounds which upon reaction produce the peroxide group.

The term "oxalyl-type" refers to a compound having at least two consecutive (adjacent) carbonyl groups.

The term "hydrogen peroxide compound" includes (1) hydrogen peroxide and (2) hydrogen peroxide-producing compounds.

We have unexpectedly discovered that the objects of this invention are obtained by admixing (1) an oxalyl-type O-oxalylhydroxylamine or another compound of the typical oxalyl-type O-acylhydroxylamine structure (as described fully below), (2) a hydroperoxide, (3) a fluorescent compound, and (4) a diluent.

The objects of this invention are obtained by employment, with other necessary chemiluminescent reactants, of an oxalyl-type O-acylhydroxylamine of the typical formula:

$$A - B - G$$

in which B is a polycarbonyl group which is a substituent of each of A and G, B being of the formula:

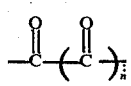

where $n'$ is an integer of at least one, in which A is a hydroxylamine compound onto which one of the terminal acyl groups of said B is substituted onto the hydroxylamine oxygen atom of said A, in which A is a substituted hydroxylamine compound derived from a hydroxyl amine selected from the group consisting of compounds of the formula:

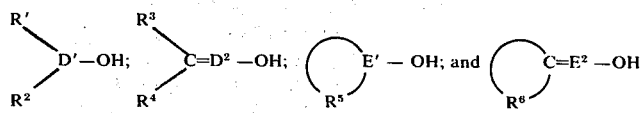

in which $n^2$ and $n^3$ each are integers of at least one, in which $D'$, $D^2$, $E'$, and $E^2$ are each a nitrogen atom, in which $R'$ and $R^3$ are each selected from the group consisting of substituted and unsubstituted alkyl, aryl, heteroaryl, acyl and aroyl, in which $R^2$ and $R^4$ each are selected from the members of $R'$ and hydrogen, in which $R^5$, $R^6$, each are selected from the group consisting of diacyl, alkylene, alkylene-diarylene, and alkylenediheteroarylene; and in which said G is selected from the group consisting of: (1) said A; (2) an alcohol (including phenols) of the formula R⁹ — O — H forming an ester of one of the terminal acyl groups of said B, in which R⁹ is selected from the group consisting of (a) electronegatively substituted saturated alkyl, (b) eletronegatively substituted aryl, (c) cyclic heteroaryl, (d) heterocyclicalkylaryl, and (e) unsaturated alkyl; and (3) an electronegatively substituted amine group selected from the group consisting of:

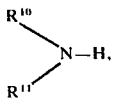

and (b) strongly electronegatively N-substituted (substituted or non-substituted) nitrogen-containing heterocyclic compounds, where the N- is attached directly to the carbonyl carbon of the oxalic acid or oxalic-type derivative, typical N-substituted nitrogen-containing heterocyclic compounds including compounds of the formula

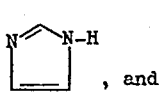, and 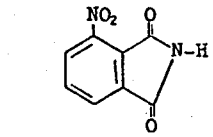

where any one or more of the heterocyclic compounds may include typical electronegative substituents such as above (a) through (c) including halogen, sulfo, oxygen-substituted phosphorous substituent, etc.; where R¹⁰ is selected from the electronegative group consisting of (a) nitro, (b) oxygenated-sulfur substituents such as

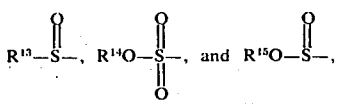

where R¹² and R¹³ are each selected from the group consisting of alkyl, aryl, cycloalkyl, heterocyclic, and polycyclic substituents, and where R¹⁴ and R¹⁵ are each selected from the group consisting of the member or R¹² and hydrogen, (c) a polyfluoroalkyl substituent such as F₃C—, F₅C₂—, F₇C₃, and the like: where R¹¹ is selected from the group consisting of the members of R¹⁰ and alkyl, aryl, cycloalkyl, heterocyclic substituents, said amine forming an acid-amide of an acyl group of said B; and (4) a 2 Z'hydro-Z²oxo-heteroaromatic compound in which Z' and Z² are integers identical in value and each Z' and Z² are each at least one, in which 2 Z'describes the number of hydro groups and Z² describes the number of oxo groups, on the heteroaromatic ring.

Specific examples of the compounds characterized by "A" of the typical formula A-B-G are as follows:

I. A substituted hydroxylamine of the typical formula:

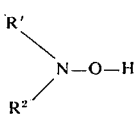

where at least one of R' and R² is an

A. alkyl group: e.g., decyl-; pentyl-; ethyl-; isopropyl-; cyclohexyl-; etc. or substituted alkyl groups, by typical substituents such as:
   a. by halogen: e.g., chloromethyl-, chloropentyl-, bromobutyl-;
   b. by carboxyl groups: e.g., carboxymethyl-, carboxyethyl-;
   c. by tertiary amino groups: e.g., methyl(phenylsulfonyl)aminoethyl-, dimethylaminoethyl-;
   d. by heterocyclic groups: e.g., pyridylethyl-, furylmethyl-, tetrahydrofurylpropyl-, acridinylethyl-;
   e. by sulfo groups: e.g., sulfomethyl-;
B. aryl group: e.g., phenyl-, naphthyl-, or substituted aryl groups by typical substituents such as:
   a. by halogen: e.g., chlorophenyl-, bromophenyl-;
   b. by acyloxy groups: e.g., benzoyloxyphenyl-;
   c. by carbonyl groups: e.g., formylphenyl-, acetylphenyl-;
   d. by carboxyl groups: e.g., carboxyphenyl-;
   e. by alkoxy groups: e.g., methoxyphenyl-;
   f. by amino groups: e.g., acetylaminophenyl-, diethylaminophenyl-;
   g. by heterocyclic groups: e.g., pyridylphenyl-, tetrahydrofurylphenyl-;
   h. by sulfo groups: e.g., sulfophenyl-, 4-sulfonaphthyl-;
   i. by carboalkoxy groups: e.g., 2-carbobutoxy-3,4,6, trichlorophenyl-;
C. heterocyclic group: e.g., pyridyl-, furyl-, acridinyl-, tetrahydrofuryl-, or substituted heterocyclic groups by typical substituents such as:
   a. by alkyl groups: e.g., methylpyridyl-;
   b. by halogen: e.g., chloropyridyl-;
   c. by acyloxy groups: e.g., acetoxypyridyl-;
   d. by carbonyl groups: e.g., formylpyridyl-;
   e. by carboxyl groups: e.g., carboxypyridyl-;
   f. by alkoxy groups: e.g., methoxyfuryl-;
   g. by amino groups: e.g., dimethylaminotetrahydrofuryl-;
   h. by sulfo groups: e.g., sulfofuryl-;
   i. by hydroxyl groups: e.g., hydroxypridyl-;
D. unsaturated alkyl and cyclic alkyl groups: e.g., vinyl-, allyl-, ethynyl-, cyclohexenyl-, isopropenyl-.

II. A substituted hydroxylamine of the typical formula:

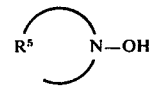

where R⁵ is a substituent defined above such as:
A. diacyl groups or electronegatively substituted diacyl groups: phthaloyl-, nitrophthaloyl-, dinitrophthaloyl-, succinyl-, oxalyl-, malonyl-, oxo-malonyl-, glutaryl-, adipyl-, malcoyl-;
B. alkylene groups or electronegatively substituted alkylene groups: ethylene-, trimethylene-,2-oxo-trimethylene-, tetramethylene-; 1-cyano-tetramethylene-, pentamethylene-, 2-oxopentamethylene-, perfluropentamethylene-, hexamethylene-;

C. alkylenediarylene or electronegatively substituted alkylenediarylene e.g., ethylenedi-p-phenylene, ethylenebis (2-nitro-p-phenylene);

D. alkylenediheteroarylene or e.g., 2,2'-ethylenedi-3-pyridinediyl.

III. Also, in the formula A — B — G described above, the "G" may typically be any of the following groups of substituents: An alcohol of the following typical formula:

$$R^9 - O - H$$

where $R^9$ represents:

A. electronegatively substituted alkyl groups substituted by typical substituents such as:
 a. by halogen: e.g., trifluoromethyl-, trichloromethyl-, perfluoroethyl-, perfluoroisopropyl-, perfluorodecyl-, 1,1,2,2-tetrafluorohexyl-;
 b. by carboxyl groups: e.g., carboxymethyl-; carboxyethyl-;
 c. by heterocyclic groups: e.g., pyridylethyl-, furylmethyl-, tetrahydrofurylpropyl-, acridinylethyl-:
 d. by sulfo groups: e.g., sulfomethyl-;

B. aryl groups: e.g., phenyl-, naphthyl-, or substituted aryl groups by typical substituents such as:
 a. by halogen: e.g., 2,4-dichlorophenyl-, pentabromophenyl-; pentafluorophenyl-;
 b. by acyloxy groups: e.g., benzoyloxyphenyl-;
 c. by carbonyl groups: e.g., formylphenyl-, acetylphenyl-;
 d. by carboxyl groups: e.g., carboxyphenyl-;
 e. by alkoxy groups: e.g., methoxyphenyl-;
 f. by nitro groups: e.g., 4-nitrophenyl-, 2,4-dinitrophenyl-;
 g. by heterocyclic groups: e.g., pyridylphenyl-, tetrahydrofurylphenyl-;
 h. by sulfo groups: e.g., sulfophenyl-, 4-sulfonaphthyl-;
 i. by cyano groups: e.g., 4-cyanophenyl-;

C. heterocyclic groups: e.g., pyridyl-, furyl-, acridinyl-, tetrahydrofuryl-, or substituted heterocyclic groups by typical substituents such as:
 a. by alkyl groups: e.g., methylpyridyl-;
 b. by halogen groups: e.g., chloropyridyl-;
 c. by acyloxy groups: e.g., acetoxypyridyl-;
 d. by carbonyl groups: e.g., formylpyridyl-;
 e. by carboxyl groups: e.g., carboxypyridyl-;
 f. by alkoxy groups: e.g., methoxyfuryl-;
 g. by amino groups: e.g., dimethylaminotetrahydrofuryl-;
 h. by sulfo groups: e.g., sulfofuryl-;
 i. by hydroxyl groups: e.g., hydroxypyridyl-;

D. unsaturated alkyl and cyclic alkyl groups: e.g., vinyl-, allyl-, ethynyl-, cyclohexenyl-, isopropenyl-.

As stated above, "G" may be an amine. Typical illustrative amino groups are as follows:

a) 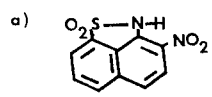  7-nitro-1,8-naphthosultam b) 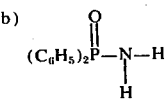  diphenylphosphinylamine c) 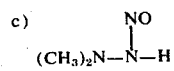  (dimethylamino)nitrosoamine d) 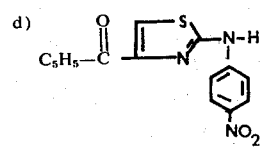  (4-benzoyl-2-thiazolyl)-(p-nitrophenyl)amine e) 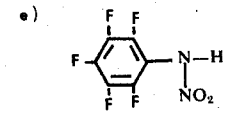  nitro(pentafluorophenyl)amine f) 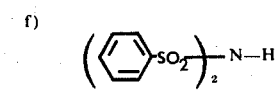  bis(phenylsulfonyl)amine g) 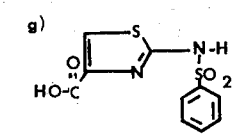  (4-carboxy-2-thiazolyl)-(phenylsulfonyl)amine h) 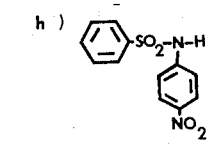  (p-nitrophenyl)-(phenylsulfonyl)amine -continued i') 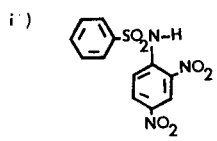 (2,4-dinitrophenyl)(phenylsulfonyl)amine j) 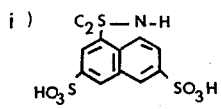 3,6-disulfo-1,8-naphthosultam k) 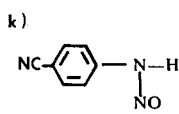 (p-cyanophenyl)nitrosoamine l) 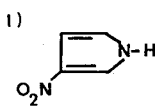 3-nitropyrrole m) 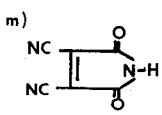 2,3-dicyanomaleimide n) 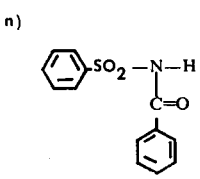 (phenylsulfonyl)benzoylamine o) 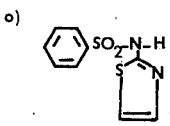 (phenylsulfonyl)-(2-thiazolyl)amine p)  (pentafluorophenyl)-(p-tolylsulfonyl)amine q) 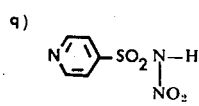 nitro(4-pyridylsulfonyl)amine r) 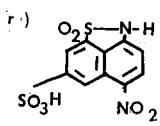 5-nitro-3-sulfo-1,8-naphthosultam s) 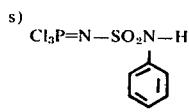 (trichlorophosphoranylidene-sulfamoyl)phenylamine t) 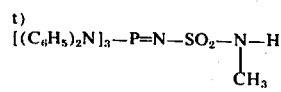 [tris(diphenylamino)phosphoranylidenesulfamoyl]methylamine u) 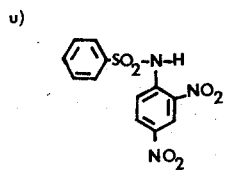 (2,4-dinitrophenyl)-(phenylsulfonyl)amine v) 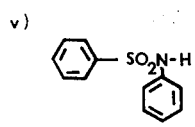 phenyl(phenylsulfonyl)amine w) 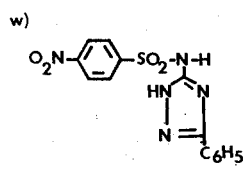 (p-nitrophenylsulfonyl)-(3-phenyl-1H-1,2,4-triazol-5-yl)amine x) 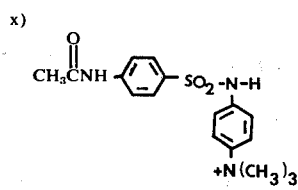 (p-acetamidophenylsulfonyl)[p-(N-bromo-N,N,N-trimethyl-ammonio)phenyl]amine As stated above "G" may be a 2 Z'hydro-Z² oxoheteroaromatic compound. Illustrative examples of this group of compounds are as follows:
1. that contain one oxo substituent as: e.g., 1,2-dihydro-2-oxoquinoline, 1,2-dihydro-2-oxopyridine, 1,5-dihydro-5-oxoquinoline, 2,3-dihydro-3-oxoisoquinoline, etc.

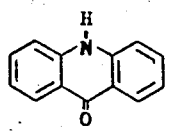

9,10-dihydro-9-oxoacridine (i.e.: acridone);
2. compounds that contain more than one oxo substituent as: e.g., 1,2,3,4-tetrahydro-2,4-dioxopyridine, 1,2,3,4,5,6-hexahydro-2,4,6-trioxopyridine, 1,2,3,4-tetrahydro-2,4-dioxoquinoline.

Other typical 2 Z'hydro-Z² oxoheteroaromatic compounds that contain at least one nitrogen and at least another heteroatom other than nitrogen, include:
1. that contain one oxo substituent as: e.g., 2,3-dihydro-3-oxoisothiazole. 2,3-dihydro-2-oxooxazole.
2. that contain more than one oxo substituent e.g., 2,3,4,5-tetrahydro-3,4-dioxoisoxazole. Typical 2 Z'hydro-Z² oxoheteroaromatic compounds that contain more than one nitrogen heteroatom include:

1. compounds that contain more than one nitrogen heteroatom but which:
   a. contain only one oxo substituent e.g., 1,2-dihydro-2-oxo-1,3,5-triazine, 1,6-dihydro-6-oxopentazine,
   b. contain more than one oxo substituent e.g., hexahydro-2,4,6-trioxo-1,3,5-triazine;
2. compounds that contain more than one nitrogen heteroatom and at least another heteroatom other than nitrogen but which
   a. contain only one oxo substituent e.g., 2,3-dihydro-3-oxofurazan. 4,5-dihydro-5-oxo-1,2,3,4-oxatriazole,
   b. contain more than one oxo substituent e.g., tetrahydro-2,5-dioxo-1,3,4-oxadiazole, tetrahydro-3,4-dioxofurazan.

Specific examples of the typical formula A - B - G defined above are as follows:

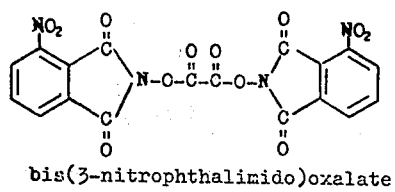

bis(3-nitrophthalimido)oxalate

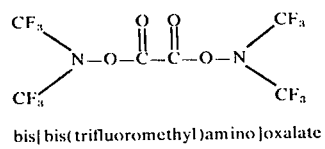
bis[bis(trifluoromethyl)amino]oxalate

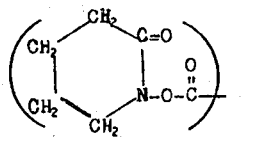
bis(2-oxopiperidino)oxalate

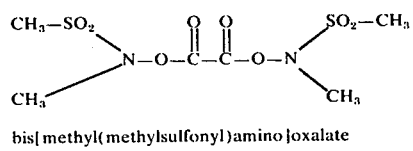
bis[methyl(methylsulfonyl)amino]oxalate

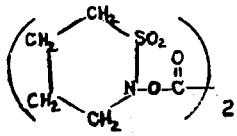
S,S,S',S'-tetraoxide of bis(tetrahydro-PH-1,2-thiazin-2-yl)oxalate

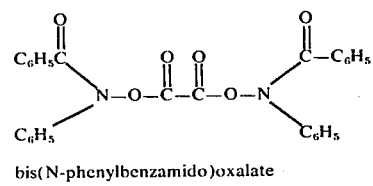
bis(N-phenylbenzamido)oxalate

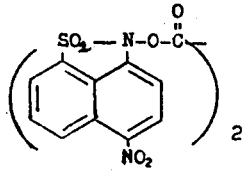
S,S,S',S'-tetraoxide of bis(5-nitro-2H-naphth[1,8-cd]isothiazol-2-yl)oxalate

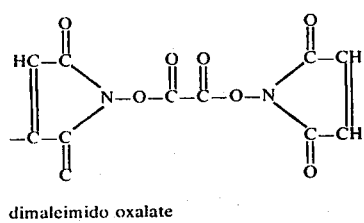
dimaleimido oxalate

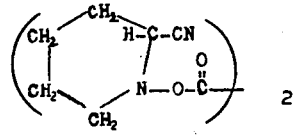
bis(2-cyanopiperidino)oxalate

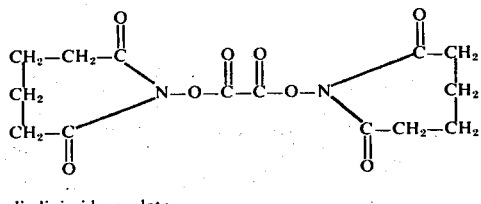
diadipimido oxalate

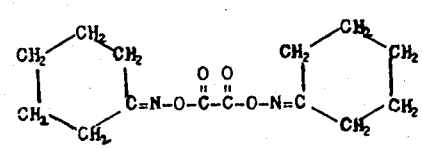
bis(cyclohexylideneamino)oxalate

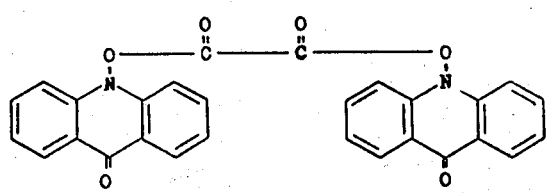
bis(9-oxo-10-acridanyl)oxalate

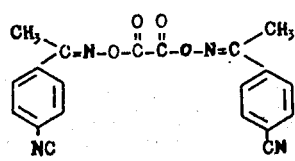
bis(p-cyano-α-methylbenzylideneamino)oxalate

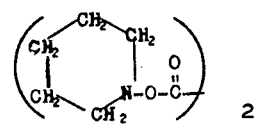
dipiperidino oxalate bis(x-methyl-2,4-dinitrobenzylideneamino)oxalate The hydroperoxide employed in the compositions and process of this invention may be obtained from any suitable peroxide compound. For example, the hydroperoxide may be employed as sodium peroxide. Alternatively, sodium perborate may be placed in aqueous solution whereby a solution of hydrogen peroxide is obtained. Obviously, hydrogen peroxide or its solution may be employed. The peroxide employed may be obtained from anhydrous hydrogen peroxide compounds such as perhydrate of urea (urea peroxide), perhydrate of pyrophosphate (sodium pyrophosphate peroxide), perhydrate of histidine (histidine peroxide), sodium perborate, and the like. Still another form in which the $H_2O_2$ may be provided in the composition is that of an anhydrous solution of $H_2O_2$ in a suitable solvent such as an ether, an ester, an aromatic hydrocarbon, etc. of the type which would provide a suitable diluent for the composition of this invention. Alternatively, the hydroperoxide employed in the composition or process could be any compound having a hydroperoxidic group, such as a hydroperoxide (ROOH) or a peroxy acid

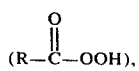

such as t-butyl hydroperoxide and perbenzoic acid. Whenever hydrogen peroxide is contemplated to be employed, any suitable compound may be substituted which will produce hydrogen peroxide.

The hydroperoxide concentration may range from about 15 molar down to about $10^{-5}$, preferably about 2 molar down to about $10^{-4}$ molar. The O-acylhydroxylamine of this invention may be added as a solid or in admixture with a suitable solid peroxide reactant or in a suitable diluent, or alternatively dissolved directly in a solution containing the peroxide reactant.

Typical diluents within the purview of the instant discovery are those that do not readily react with a peroxide such as hydrogen peroxide, and which do not readily react with an O-acylhydroxylamine.

Although the addition of water is not necessary for the production of chemiluminescent light in certain embodiments according to the present invention, water can serve as the sole diluent or partial diluent. The term "water", as used herein, includes water-producing compounds such as hydrates. In addition, however, either one or more diluents may be included with or in the place of the water, as long as the peroxide employed is at least partially soluble in the diluents(s), such as, for example, at least 1/10 gram of $H_2O_2$ per liter of diluent. The following are illustrative of the additional diluents or solvents which may be employed: non-cyclic or cyclic ethers, such as diethyl ether, diamyl ether, diphenyl ether, anisole, tetrahydrofuran, dioxane, and the like; esters such as ethyl acetate, propyl formate, amyl acetate, dimethyl phthalate, diethyl phthalate, methyl benzoate, and the like; aromatic hydrocarbons, such as benzene, xylene, toluene, and the like.

When water is used as the sole diluent in certain chemiluminescent compositions, additives can be used optionally to enhance the solubility of the oxalate and of the fluorescer in this reaction medium. Such additives are: ammonium, phosphonium salts, amine oxides and other surface active agents e.g., tetrabutylammonium perchlorate, tetrabutylammonium salicylate, bis(2-hydroxyethyl) octadecylamine oxide, bis(2-hydroxyethyl) cocoamine oxide, tetrabutylphosphonium hexafluorophosphate and tetrabutylphosphonium perchlorate.

The fluorescent compounds contemplated herein are numerous; and they may be defined broadly as those which do not readily react on contact with the peroxide employed in this invention, such as hydrogen peroxide; likewise, they do not readily react on contact with the ester of oxalic acid. Typical suitable fluorescent compounds for use in the present invention are those which have a spectral emission falling between 330 millimicrons and 800 millimicrons and which are at least partially soluble in any of the above diluents, if such diluent is employed. Among these are the conjugated polycyclic aromatic compounds having at least 3 fused rings, such as: anthracene, substituted anthracene, benzanthracene, phenanthrene, substituted phenanthrene, naphthacene, substituted naphthacene, pentacene, substituted pentacene, and the like. Typical substituents for all of these are phenyl, lower alkyl, chloro, bromo, cyano, alkoxy ($C_1$–$C_{16}$), and other like substituents which do not interfere with the light-generating reaction, contemplated herein.

Numerous other fluorescent compounds having the properties given hereinabove are well known in the art. Many of these are fully described in "Fluorescence and Phosphorescence", by Peter Pringsheim, Interscience Publishers, Inc. New York, N.Y. 1949. Other fluorescers are described in "The Colour Index", Second Edition, Volume 2, The American Association of Textile Chemists and Colorists, 1956, pp. 2907–2923. While only typical fluorescent compounds are listed hereinabove, the person skilled in the art is fully aware of the fact that this invention is not so restricted and that numerous other fluorescent compounds having similar properties are contemplated for use herein.

It should be noted, however, that although a fluorescent compound is necessary to obtain the production of light, the fluorescent compound is not necessary to obtain a chemical reaction and chemical energy release. Also, a fluorescent O-acylhydroxylamine such as phthalimido 3,6,8-trisulfo-2-napthyl oxalate does not require a separate fluorescent compound to obtain light. Thus, a reactant including a fluorescent O-acylhydroxylamine would thereby "include at least one fluorescent compound."

It has been found that the molar (moles per liter of diluent) concentrations of the major components of the novel composition herein described may vary considerably. It is only necessary that components be in sufficient concentration to obtain chemiluminescence. The O-acylhydroxylamine molar concentration normally is in the range of at least about $10^{-7}$ to 5 molar, preferably in the range of at least about $10^{-4}$ to about 1 molar; the fluorescent compound is present in the range from about $10^{-5}$ to 5, preferably $10^{-4}$ to $10^{-1}$; and the water or other diluent must be present in a sufficient amount to form at least a partial solution of the reactants involved in the chemiluminescent reaction. There is no known maximum limit on the concentration of O-acylhydroxylamine employed in the reaction. The ester may serve as either the sole diluent or a partial diluent.

The ingredients of the composition of this invention, may be admixed in a single stage of admixing or in a sequence of steps of admixing the separate ingredients. Accordingly, alternative compositions may be prepared which may be stored over a period of time and which may be admixed with the final ingredient at a time when the chemiluminescent lighting is desired. For example, one such composition would be a composition which includes an O-acylhydroxylamine and a fluorescent compound but which does not include a peroxide compound. Another alternative composition would be a composition which includes the fluorescent compound and a peroxide, but which does not include the O-acylhydroxylamine. Another alternative composition would be a solid composition which includes a solid O-acylhydroxylamine and a solid hydroperoxide compound, and possibly additionally includes a solid fluorescent compound, but which does not include a diluent. Obviously the preferred composition which would be less than all necessary components to produce a chemiluminescent light would be a composition which would be substantially stable to a practical degree over an extended period of time; otherwise, there would be no real advantage in forming a chemiluminescent reactant to be employed in a subsequent chemiluminescent reaction.

The wavelength of the light emitted by chemiluminescence of the compositions of this invention, i.e., the color of the light emitted, may be varied by the addition of any one or more energy transfer agents (fluorescers) such as the known fluorescent compounds discussed at length above.

The wavelength of the light emitted by the composition of this invention will vary, depending upon the particular fluorescent component employed in the reaction.

Although in the process of obtaining chemiluminescent light according to this invention, it is normally not necessary to employ a specific order of sequence of steps in the adding of the individual ingredients of the inventive chemiluminescent composition, it has been found that the fluorescent component preferably should be already in the reaction mixture at the time of addition of the last component necessary to bring about the chemical reaction and the concurrent release of chemical energy.

Additionally, it has been found that the superior intensity of chemiluminescence is obtained when the final mixture producing the luminescence is maintained at a temperature of between about −40°C. and 75°C., preferably between about 20°C. and 50°C.; however, the luminescence of Applicant's process is not limited to these ranges. However, temperature is not critical.

Additionally, the composition and the process which obtains preferred optimum chemiluminescent light intensity employs a base in an amount sufficient to produce a basic pH. However, the preferred extended lifetime is obtained under about neutral conditions. Any suitable base which does not interfere with the chemiluminescent composition and process of this invention may be employed.

A wide variety of organic and inorganic bases is contemplated, typical bases being: sodium hydroxide, potassium hydroxide, potassium tertiary butoxide, sodium ethoxide, sodium methoxide, ammonium hydroxide, tetrabutyl ammonium hydroxide, and triphenyl methide; Lewis bases, including pyridine, triethylamine, quinoline, and the like. Weak bases including sodium salicylate, tetrabutyl-ammonium salicylate and those that are described in detail in the copending commonly assigned application Ser. No. 813848, filed on April 7, 1969.

The composition and the process which obtains chemiluminescent light may optionally employ an acid in an amount sufficient to produce an acidic pH. However, the presence of acid is not essential to obtain chemiluminescence.

The lifetime and the intensity of the chemiluminescent light can be regulated by the use of certain regulators such as:

1. By the addition of base to the chemiluminescent composition. Both the strength and the concentration of the base are critical for purposes of regulation.
2. By the variation of hydroperoxide. Both the type and the concentration of hydroperoxide are critical for the purposes of regulation.
3. By the addition of water.
4. By the addition of a catalyst which changes the rate of reaction of hydroperoxide with the O-acylhydroxylamine. Catalysts which accomplish that objective include those described in M. L. Bender, "Chem. Revs.", Vol 60, p.53 (1960).

The following examples are intended to illustrate the present invention and are in no way intended to limit the invention except as limited in the appended claims.

EXAMPLE I

Preparation of Diphthalimido Oxalate (i.e., an acylhydroxylamine)

1.63 g (0.01 mole) N-hydroxyphthalimide is dissolved in 100 ml freshly distilled 1,2-dimethoxyethane. To the rapidly stirred solution 0.43 ml (0.005 mole) oxalyl chloride and 1.4 ml (0.01 mole) triethylamine is added at 25°C. After 1 hour stirring the mixture is evaporated to dryness under vacuum and the solid residue is digested 3 times with 30 ml portions of chloroform to obtain the product, white crystals, m.p. 233°–4°C. in 42% yield.

Anal. calcd. for $C_{18}H_8O_8$: C, 56.85; H, 2.12; N, 7.37. Found: C, 56.10; H, 2.00, N, 7.45.

EXAMPLE II

The tests of Table I were carried out as follows:

A. Approximately 3–5 mg of the compound of Example I to be tested is added to a 5 ml solution of about 1 mg 9,10-diphenylanthracene (DPA) and 0.2 ml anhydrous $H_2O_2$ in anhydrous 1,2-dimethoxyethane maintained at 25°C.

B. Approximately 3–5 mg of the compound of Example I to be tested is added to a 5 ml slurry of 1 mg DPA, 0.2 g KOH (1 pellet) and 0.2 ml anhydrous $H_2O_2$ in anhydrous 1,2-dimethoxyethane maintained at 25°C.

C. Part C is conducted the same as test A except that approximately 0.1 ml water is added prior to the addition of the compound being tested.

D. Approximately 3–5 mg of the oxalate compound of Example I to be tested is added to a 5 ml solution of 1 mg DPA and 0.2 ml $CH_3SO_3H$ in 1,2-dimethoxyethane containing 5% water and maintained at 25°C. About 0.2 ml 98% $H_2O_2$ is added immediately.

Qualitative intensities are based on the oxalyl chloride, hydrogen peroxide reaction taken as strong(S). Other designations are M = medium; W = weak; VW = very weak, barely visible.

The compound is subjected to qualitative chemiluminescent tests as shown in Table I.

TABLE I

| O-acylhydroxyl-amine | Tests[a] | | | |
|---|---|---|---|---|
| | A Anhyd.$H_2O_2$ | B $H_2O_2$+HOH | C $H_2O_2$+$H_2O$ | D $H_2O_2$+$H_3O^+$ |
| (phthalimide-N–O–C(O)– structure)$_2$ | S (long) | S (fast) | MS (long) | W (long) |

EXAMPLE III

Employing the diphthalamido oxalate of Example I, tests A through E are conducted to determine the lifetime, the quantum yield and the radiation capacity employing dimethyl phthalate solvent, and varying amounts of the oxalate and the hydrogen peroxide. As a fluorescer, 9,10-diphenylanthracene is employed. All measurements are carried out at about 25°C. The lifetime is expressed in terms of ($t_{1/4}$ $I_{max}$) the time required for the light intensity to decrease to one quarter of its minimum value. For Part D, 0.015 mole $l^{-1}$ of water is added to the reaction. For Part E, 8.3 × $10^{-6}$ mole $l^{-1}$ of triethylamine is added to the reaction.

For Parts F and G the procedure is the same as for the above Examples A through C, except for employing propylene carbonate as the solvent, and varying the relative quantities of reactants.

The concentrations of the oxalate and hydrogen peroxide are shown in Table II below.

Quantitative Measurements of the Chemiluminescence carried out in the two different solvents are shown in Table II.

EXAMPLE V

Tests described in Example IV are repeated but t-butyl hydroperoxide is used in the place of 4-nitroperoxybenzoic acid. The results of the test are as follows:
A. Very weak chemiluminescence is observed.
B. Medium chemiluminescence is observed.
C. Very weak chemiluminescence is observed.
D. No substantial chemiluminescence is observed.

EXAMPLE VI

Preparation of dimaleimido oxalate is carried out according to the procedure shown in Example I except N-hydroxy-maleimide is used in the place of N-hydroxy phthalimide.

EXAMPLE VII

Preparation of dipiperidino oxalate.

TABLE II

Chemiluminescence Quantum Yield and Radiation Capacity of Diphthalimido Oxalate

| Example III Part | O-oxalyl-hydroxylamine (mole $l^{-1}$) | $H_2O_2$ (mole $l^{-1}$) | $t_{1/4}I_{max}$ (min) | Quantum Yield (einstein $mole^{-1}$ × $10^2$) | Radiation Capacity (einstein $l^{-1}$ × $10^4$) |
|---|---|---|---|---|---|
| A | 0.001 | 0.024 | 94.0 | 8.7 | 0.9 |
| B | 0.010 | 0.0024 | 307.0 | 2.3 | 2.3 |
| C | 0.010 | 0.0090 | 269.0 | 1.9 | 1.9 |
| D | 0.010 | 0.0090 | 169.0 | 2.7 | 2.7 |
| E | 0.010 | 0.0090 | 184.0 | 4.3 | 4.3 |
| F | 0.0010 | 0.034 | 6.7 | 2.64 | 0.26 |
| G | 0.0100 | 0.034 | 10.1 | 1.41 | 1.41 |

EXAMPLE IV

Diphthalimido oxalate is tested for chemiluminescence in a reaction with hydroperoxides other than hydrogen peroxide. The tests carried out are as follows:

A. Approximately, 3 mg diphthalimido oxalate is added to a 5 ml solution of 1 mg 9,10-diphenylanthracene (DPA) and 25 mg 4-nitroperoxybenzoic acid in 1,2-dimethoxyethane (DME) maintained at about 25°C. Weak chemiluminescence is observed.

B. Test is similar to test A except 0.2 g KOH is also added. Medium weak chemiluminescence is observed.

C. Test is similar to test A except 0.1 ml water is also added. No substantial chemiluminescence is observed.

D. Test is similar to test A except 0.1 ml methanesulfonic acid is also added. No substantial chemiluminescence is observed.

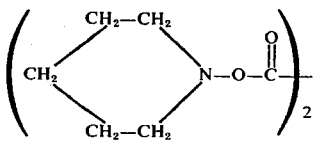

is carried out according to the procedure shown in Example I except N-hydroxy piperidine is used in the place of N-hydroxy phthalimide.

EXAMPLE VIII

The preparation of disuccinimido oxalate: to a mixture of 11.5 g (0.1 mole) N-hydroxy succinimide 200 ml benzene and 200 ml anhydrous ether. 13.95 ml (0.1 mole) triethylamine and 4.26 ml (0.05 mole) oxalyl chloride were added to obtain a brown slurry which was diluted with 500 ml benzene, stirred for 90 minutes and filtered to obtain a brown solid. This solid was reslurried with 80 ml chloroform filtered and washed with two 30 ml portions of chloroform to obtain a light brown solid which was reslurried again with 800 ml ethyl acetate filtered and washed with two portions of 40 ml acetone and dried to obtain approximately 4.5 g (16% of theory) light brown hydroscopic solid product mp. 176°C (decomposes).

Anal. calcd. for $C_{10}H_8O_8N_2$: C, 42.26; H, 2.84, N, 9.86. Found: C, 42.37: H, 3.16, N, 9.78.

EXAMPLE IX

Qualitative chemiluminescence tests of disuccinimido oxalate in tetrahydrofuran solvent: A very bright green chemiluminescent light emission is obtained when approximately 3 mg disuccinimido oxalate is added to a 2 ml solution of 0.3 molar hydrogen peroxide and 0.001 molar 9,10-bis(phenylethnyl) anthracene in tetrahydrofuran.

EXAMPLE X

Qualitative chemiluminescence tests of disuccinimido oxalate in 3-methyl-3-pentanol solvent: Three experiments were carried out as described in Example IX except a different fluorescer was used in each case, 9,10-bis(phenylethynyl) anthracene, N-methylacridinium chloride and sodium fluorescein. Moderately weak light emissions were obtained in the presence of all three fluorescers in 3-methyl-3-pentanol a tertiary alcohol solvent.

EXAMPLE XI

Qualitative chemiluminescence tests of disuccinimido oxalate in water solution: A bright chemiluminescent light emission is obtained when approximately 3 mg disuccinimido oxalate is added to 5 ml solution of 1 mg sodium fluorescein, 3 mg tetrabutylammonium salicylate and 0.4 ml 98% hydrogen peroxide in water. The sodium fluorescein dissolves slowly and should be dissolved in water first by mild warming for best results. Sodium salicylate may replace tetrabutyl-ammonium salicylate.

Chemiluminescent light emission is also obtained when sodium fluorescein is replaced by 9,10-bis(phenylethyuyl) anthracene provided that approximately 0.5 g tetrabutylammonium perchlorate is added to the solution.

It is within the scope of this invention to make such modifications of the compositions and processes disclosed herein as would be obvious to a person of ordinary skill in this art, and it is to be understood that the examples illustrating this invention are intended to limit the invention only insofar as is stated in the specification and as the following claims are limited. Also, it is within the scope of this invention to form an apparatus or article such as a container which, for example, may be either (1) a substantially insoluble or alternatively (2) a dissolvable capsule in which the reactant or composition of this invention is substantially enclosed for subsequent reaction with other ingredients necessary to produce chemiluminescent light.

We claim:
1. Diphthalimido oxalate.
2. Disuccinimido oxalate.
3. Dimaleimido oxalate.

* * * * *